(12) United States Patent
Hayashi et al.

(10) Patent No.: US 10,597,540 B2
(45) Date of Patent: Mar. 24, 2020

(54) SURFACE TREATMENT AGENT FOR SURFACE CONFIGURED FROM INORGANIC MATERIAL, TOOL AND DEVICE HAVING MODIFIED SURFACE, AND METHOD FOR MANUFACTURING TOOL AND DEVICE

(71) Applicants: JSR CORPORATION, Minato-ku (JP); JSR LIFE SCIENCES CORPORATION, Minato-ku (JP)

(72) Inventors: Naoki Hayashi, Minato-ku (JP); Tomoki Itooka, Minato-ku (JP); Shin-ya Omote, Minato-ku (JP); Kazuhiro Iso, Minato-ku (JP)

(73) Assignees: JSR CORPORATION, Tokyo (JP); JSR LIFE SCIENCES CORPORATION, Tokyo (JP)

( * ) Notice: Subject to any disclaimer, the term of this patent is extended or adjusted under 35 U.S.C. 154(b) by 139 days.

(21) Appl. No.: 14/893,585

(22) PCT Filed: May 27, 2014

(86) PCT No.: PCT/JP2014/063939
§ 371 (c)(1),
(2) Date: Nov. 24, 2015

(87) PCT Pub. No.: WO2014/192731
PCT Pub. Date: Dec. 4, 2014

(65) Prior Publication Data
US 2016/0102213 A1     Apr. 14, 2016

(30) Foreign Application Priority Data

May 27, 2013   (JP) ................. 2013-111087

(51) Int. Cl.
| | |
|---|---|
| *C09D 5/16* | (2006.01) |
| *C03C 17/32* | (2006.01) |
| *C08F 220/28* | (2006.01) |
| *C09D 7/65* | (2018.01) |
| *C09D 133/14* | (2006.01) |
| *C09D 133/02* | (2006.01) |
| *C09D 133/04* | (2006.01) |
| *C08L 33/14* | (2006.01) |
| *C08L 33/04* | (2006.01) |
| *C08L 33/02* | (2006.01) |
| *C03C 17/28* | (2006.01) |
| *C08F 220/22* | (2006.01) |
| *C08F 220/34* | (2006.01) |

(Continued)

(52) U.S. Cl.
CPC .......... *C09D 5/1637* (2013.01); *A61L 17/145* (2013.01); *A61L 27/02* (2013.01); *A61L 27/34* (2013.01); *A61L 29/02* (2013.01); *A61L 29/085* (2013.01); *A61L 31/02* (2013.01); *A61L 31/10* (2013.01); *C03C 17/32* (2013.01); *C08F 220/28* (2013.01); *C09D 7/65* (2018.01); *C09D 133/14* (2013.01); *G01N 33/54393* (2013.01); *B32B 7/04* (2013.01); *B32B 2255/06* (2013.01); *B32B 2255/26* (2013.01); *B32B 2535/00* (2013.01); *C03C 17/00* (2013.01); *C03C 17/28* (2013.01); *C03C 2217/70* (2013.01); *C08F 220/22* (2013.01); *C08F 220/34* (2013.01); *C08F 220/36* (2013.01); *C08F 220/58* (2013.01); *C08F 2220/282* (2013.01); *C08F 2220/286* (2013.01); *C08L 33/02* (2013.01); *C08L 33/04* (2013.01); *C08L 33/14* (2013.01); *C09D 5/16* (2013.01); *C09D 5/1656* (2013.01); *C09D 5/1668* (2013.01); *C09D 133/02* (2013.01); *C09D 133/04* (2013.01); *G01N 33/543* (2013.01); *Y10T 428/31678* (2015.04); *Y10T 428/31692* (2015.04); *Y10T 428/31699* (2015.04)

(58) Field of Classification Search
None
See application file for complete search history.

(56) References Cited

U.S. PATENT DOCUMENTS

| | | | | |
|---|---|---|---|---|
| 3,671,502 A | * | 6/1972 | Samour | .............. C08F 220/28 526/212 |
| 5,645,883 A | * | 7/1997 | Russell | ............... A61L 27/34 427/2.25 |

(Continued)

FOREIGN PATENT DOCUMENTS

| | | |
|---|---|---|
| CN | 1954004 A | 4/2007 |
| CN | 101430333 A | 5/2009 |

(Continued)

OTHER PUBLICATIONS

"Wikipedia—Chemisorption" (https://en.wikipedia.org/wiki/Chemisorption) (webpage retrieved Feb. 13, 2019). (Year: 2019).*

(Continued)

*Primary Examiner* — Vivian Chen
(74) *Attorney, Agent, or Firm* — Oblon, McClelland, Maier & Neustadt, L.L.P.

(57) ABSTRACT

A surface treatment method for treating a surface formed of an inorganic material by using a polymer is provided. The polymer contains a repeating unit (A) having a cationic group with a particular structure in a side chain thereof and a repeating unit (B) having a group of a particular structure in a side chain thereof. Also provided are a tool and a device having a modified surface, and a method for producing the tool and the device.

4 Claims, No Drawings

(51) Int. Cl.

| | | |
|---|---|---|
| C08F 220/36 | (2006.01) | |
| C03C 17/00 | (2006.01) | |
| C08F 220/58 | (2006.01) | |
| B32B 7/04 | (2019.01) | |
| A61L 27/02 | (2006.01) | |
| A61L 31/02 | (2006.01) | |
| A61L 31/10 | (2006.01) | |
| A61L 29/02 | (2006.01) | |
| A61L 29/08 | (2006.01) | |
| A61L 27/34 | (2006.01) | |
| A61L 17/14 | (2006.01) | |
| G01N 33/543 | (2006.01) | |

(56) References Cited

U.S. PATENT DOCUMENTS

| | | | | | |
|---|---|---|---|---|---|
| 5,648,442 | A | * | 7/1997 | Bowers | C08F 246/00 526/277 |
| 5,705,583 | A | * | 1/1998 | Bowers | C07F 9/091 427/407.1 |
| 5,728,437 | A | * | 3/1998 | Nygren | A61L 33/06 428/35.6 |
| 5,739,236 | A | * | 4/1998 | Bowers | C08F 246/00 526/245 |
| 6,087,462 | A | * | 7/2000 | Bowers | C08F 246/00 526/277 |
| 6,090,901 | A | * | 7/2000 | Bowers | C08F 230/02 526/277 |
| 6,225,431 | B1 | * | 5/2001 | Bowers | C07F 9/091 427/384 |
| 6,251,964 | B1 | * | 6/2001 | Porssa | A61L 33/0029 523/105 |
| 6,284,854 | B1 | * | 9/2001 | Bowers | C07F 9/091 526/242 |
| 2003/0086957 | A1 | | 5/2003 | Hughes et al. | |
| 2004/0197585 | A1 | | 10/2004 | Hughes et al. | |
| 2004/0208985 | A1 | * | 10/2004 | Rowan | A61L 27/34 427/2.25 |
| 2005/0004661 | A1 | * | 1/2005 | Lewis | A61L 31/10 623/1.42 |
| 2005/0008603 | A1 | * | 1/2005 | Marchant | A61L 27/34 424/70.14 |
| 2006/0079958 | A1 | * | 4/2006 | Stratford | A61L 29/085 623/1.46 |
| 2007/0166344 | A1 | * | 7/2007 | Qu | A61L 15/46 424/423 |
| 2008/0139746 | A1 | * | 6/2008 | Pacetti | A61L 27/34 525/188 |
| 2008/0262181 | A1 | | 10/2008 | Kitano et al. | |
| 2008/0262614 | A1 | * | 10/2008 | Marchant | A61L 27/34 623/11.11 |
| 2009/0317443 | A1 | * | 12/2009 | Willis | A61L 31/10 424/423 |
| 2010/0152708 | A1 | * | 6/2010 | Li | A61L 27/34 604/523 |
| 2011/0305872 | A1 | * | 12/2011 | Li | A61L 29/06 428/141 |
| 2011/0305881 | A1 | * | 12/2011 | Schultz | A61L 33/0088 428/195.1 |
| 2011/0305898 | A1 | * | 12/2011 | Zhang | A61L 27/34 428/336 |
| 2012/0114571 | A1 | * | 5/2012 | Klug | A61K 8/86 424/59 |

FOREIGN PATENT DOCUMENTS

| | | | |
|---|---|---|---|
| CN | 102653573 A | | 9/2012 |
| JP | 2000 206471 | | 7/2000 |
| JP | 2003 520107 | | 7/2003 |
| JP | 2006 84393 | | 3/2006 |
| JP | 2009-133809 A | * | 6/2009 |
| JP | 2012-189605 A | * | 10/2012 |
| JP | 2013 70796 | | 4/2013 |
| WO | 2010 032846 | | 3/2010 |

OTHER PUBLICATIONS

"Wikipedia—Physisorption" (https://en.wikipedia.org/wiki/Physisorption) (webpage retrieved Feb. 13, 2019). (Year: 2019).*

Lin, C.Y. et al. "Micro/nano-structuring of medical stainless steel using femtosecond laser pulses". Physics Procedia 39 (2010) 661-668. (Year: 2012).*

Luo, B.H. et al. "Preparation of hydrophobic surface on steel by patterning using laser ablation process". Surface & Coatings Technology 204 (2010) 1180-1185. (Year: 2010).*

Kam, D.H. et al. "Control of the wetting properties of an AISI 316L stainless steel surface by fenntosecond laser-induced surface modification". Journal of Micromechanics and Microengineering 22 (2012) 105019. (Year: 2012).*

Lui, W.P. et al. "Hydrophobic surface fabricated by laser interference lithography." 2012 International Conference on Manipulation, Manufacturing, and Measurement on the Nanoscale (Aug.29-Sep. 1, 2012). (Year: 2012).*

Noh, Sooryun et al. "Formation and characterization of hydrophobic glass surface treated by atmospheric pressure He/CH4 plasma". Journal of Applied Physics 115 043307 (Jan. 2014). (Year: 2014).*

Combined Chinese Office Action and Search Report dated Oct. 21, 2016 in Chinese Patent Application No. 201480028676.X (with partial unedited computer generated English language translation and English translation of categories of cited documents).

International Search Report dated Sep. 2, 2014 in PCT/JP14/063939 Filed May 27, 2014.

* cited by examiner

SURFACE TREATMENT AGENT FOR SURFACE CONFIGURED FROM INORGANIC MATERIAL, TOOL AND DEVICE HAVING MODIFIED SURFACE, AND METHOD FOR MANUFACTURING TOOL AND DEVICE

TECHNICAL FIELD

The present invention relates to a surface treatment agent for a surface formed of an inorganic material, a tool and a device having a modified surface, and a method for producing the tool and the device.

BACKGROUND ART

A method for measuring a bio-related substance by using various reagents is widely used for clinical tests, diagnostic agents, or various studies, for example. As a method for detecting the bio-related substance, for example, there are methods of utilizing enzymatic coloration, utilizing fluorescence or chemical luminescence, utilizing color comparison due to a shift in the absorption wavelength of light of a substance, and utilizing turbidity using latex as an index. However, in any detection methods, a problem arises in which biomolecules or cells such as protein, lipid, and nucleic acids in a blood serum, or a protein, a luminescent substrate, or a light absorbing substance in a measurement reagent or the like is non-specifically adsorbed to a solid phase such as glass or plastic, a container, or a tool or the like, and thus this adsorbed substance causes noise, thereby reducing the sensitivity of the detection methods.

Thus, generally, in order to suppress non-specific adsorption as described above, for example, a measure to treat the surface of a solid phase, a container, or a tool, with a biological substance such as albumin, casein, or gelatin has been devised.

However, the biological substance as described above does not have a sufficient effect for suppressing non-specific adsorption with respect to a surface formed of an inorganic material such as glass, and there is also concern that biological contamination typified by BSE may occur.

Therefore, the development of the surface treatment agent for a surface formed of an inorganic material by chemical synthesis has been desired, and for example, a surface treatment agent having poly(2-methacryloyloxyethyl phosphorylcholine) as an effective ingredient has been reported (Patent Literatures 1 to 3).

CITATION LIST

Patent Literature

Patent Literature 1: JP-A 2006-84393
Patent Literature 2: WO-A 2010/032846
Patent Literature 3: JP-A 2000-206471

SUMMARY OF THE INVENTION

Problem To be Solved by the Invention

An object of the present invention is to provide a surface treatment agent having an excellent effect for suppressing non-specific adsorption with respect to a surface formed of an inorganic material and also having excellent peel resistance, a tool and a device having a modified surface, and a method for producing the tool and the device.

Means for Solving the Problem

The present inventors conducted intensive studies, and as a result, found that a polymer having a repeating unit including a specific cationic group in a side chain thereof and a repeating unit including a specific (poly)oxyalkylene group in a side chain thereof has an excellent effect for suppressing non-specific adsorption with respect to a surface formed of an inorganic material. Thus, the present invention has been accomplished.

That is, according to the present invention, there is provided a surface treatment agent for a surface formed of an inorganic material, comprising a polymer having the following repeating units (A) and (B).

(A) A repeating unit including a cationic group represented by the following Formula (1) in a side chain thereof

[In Formula (1), $R^1$ and $R^2$ each independently represents an organic group with 1 to 10 carbon atoms.]

(B) A repeating unit including a group represented by the following Formula (2) in a side chain thereof

[In Formula (2), $R^3$ represents an alkanediyl group with 2 to 8 carbon atoms, $R^4$ represents a hydrogen atom or an organic group with 1 to 40 carbon atoms, and n has an average value of 1 or more.]

Furthermore, the present invention is to provide a tool having a modified surface, including the polymer having the repeating units (A) and (B) described above on at least a part of the surface formed of an inorganic material.

Furthermore, the present invention is to provide a method for producing a tool having a modified surface, including a step of coating at least a part of the surface formed of an inorganic material with a polymer having the repeating units (A) and (B) described above.

Furthermore, the present invention is to provide a device having a modified surface, including the polymer having the repeating units (A) and (B) described above on at least a part of the surface formed of an inorganic material.

Furthermore, the present invention is to provide a method for producing a device having a modified surface, including a step of coating at least a part of the surface formed of an inorganic material with a polymer having the repeating units (A) and (B) described above.

Furthermore, the present invention is to provide a method for modifying a surface, including a step of coating at least a part of the surface formed of an inorganic material with a polymer having the repeating units (A) and (B) described above.

Effects of the Invention

The surface treatment agent of the present invention has an excellent effect for suppressing non-specific adsorption with respect to a surface formed of an inorganic material, and also has excellent peel resistance.

Therefore, in the tool and the device of the present invention, non-specific adsorption with respect to a surface formed of an inorganic material is suppressed, and also this effect is less likely to decrease. According to the producing method of the present invention, it is possible to simply and easily manufacture a tool and a device in which non-specific adsorption with respect to a surface formed of an inorganic material is suppressed and also this effect is less likely to decrease.

DETAILED DESCRIPTION OF THE INVENTION

[Surface Treatment Agent]

A surface treatment agent for a surface formed of an inorganic material of the present invention includes a polymer having the repeating units (A) and (B) described above.

<Repeating Unit (A)>

The repeating unit (A) includes a cationic group represented by the following Formula (1) in a side chain thereof.

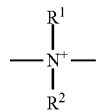
(1)

[In Formula (1), $R^1$ and $R^2$ each independently represents an organic group with 1 to 10 carbon atoms.]

The number of carbon atoms of the organic groups represented by $R^1$ and $R^2$ in the above Formula (1) is preferably 1 to 6, more preferably 1 to 3, and further preferably 1 or 2.

As the organic group, a hydrocarbon group is exemplified, and an aliphatic hydrocarbon group is preferable. The aliphatic hydrocarbon group may be a linear chain or a branched chain, and examples thereof include alkyl groups such as a methyl group, an ethyl group, an n-propyl group, an isopropyl group, an n-butyl group, an isobutyl group, a sec-butyl group, a tert-butyl group, a pentyl group, and a hexyl group.

Furthermore, as the repeating unit (A), a repeating unit represented by the following Formula (3) is preferable from the viewpoints of an effect for suppressing non-specific adsorption, adsorptivity to a base material, peel resistance, and coatability.

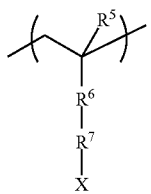
(3)

[In Formula (3), $R^5$ represents a hydrogen atom or a methyl group, $R^6$ represents —O—, *—(C=O)—O—, *—(C=O)—NR$^8$—, *—NR$^8$—(C=O)— ($R^8$ represents a hydrogen atom or an organic group with 1 to 10 carbon atoms, and * denotes the position of bonding to the carbon atom to which $R^5$ is bonded in Formula (3)), or a phenylene group, $R^7$ represents a divalent organic group with 1 to 8 carbon atoms, and X represents a monovalent group represented by the following Formula (4-1) or (4-2).

(4-1)

[In Formula (4-1), $R^9$ represents an organic group with 1 to 10 carbon atoms which has an anionic group as a substituent, or an organic group with 1 to 10 carbon atoms, and $R^1$ and $R^2$ have the same meaning as described above.]

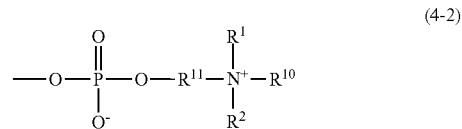
(4-2)

[In Formula (4-2), $R^{10}$ represents an organic group with 1 to 10 carbon atoms, $R^{11}$ represents a divalent organic group with 1 to 8 carbon atoms, and $R^1$ and $R^2$ have the same meaning as described above.]]

In the above Formula (3), $R^6$ represents —O—, *—(C=O)—O—, *—(C=O)—NR$^8$—, *—NR$^8$—(C=O)—, or a phenylene group. Examples of such a phenylene group include a 1,2-phenylene group, a 1,3-phenylene group, and a 1,4-phenylene group.

Furthermore, $R^8$ described above represents a hydrogen atom or an organic group with 1 to 10 carbon atoms. Such an organic group with 1 to 10 carbon atoms is the same as the organic group with 1 to 10 carbon atoms represented by $R^1$ described above.

As $R^6$ as described above, *—(C=O)—O— and *—(C=O)—NR$^8$— are preferable, *—(C=O)—NR$^8$— is more preferable, and *—(C=O)—NH— is further preferable.

The number of carbon atoms of the divalent organic group represented by $R^7$ in the above Formula (3) is preferably 1 to 6, more preferably 1 to 4, and further preferably 2 or 3.

As the divalent organic group, a divalent hydrocarbon group is exemplified, and a divalent aliphatic hydrocarbon group is preferable. The divalent aliphatic hydrocarbon group may be a linear chain or a branched chain, and examples thereof include alkanediyl groups such as a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, and a hexane-1,6-diyl group.

In the above Formula (4-1), $R^9$ represents an organic group with 1 to 10 carbon atoms which has an anionic group as a substituent or an organic group with 1 to 10 carbon atoms. From the viewpoints of an effect for suppressing non-specific adsorption and peel resistance, an organic group with 1 to 10 carbon atoms is preferable.

Furthermore, the number of carbon atoms of the organic group in $R^9$ is 1 to 10, and is preferably 1 to 7, more preferably 1 to 3, and further preferably 1 or 2.

Furthermore, as the organic group, a hydrocarbon group is exemplified, an aliphatic hydrocarbon group, an aromatic hydrocarbon group, and a hydrocarbon group where they are together linked are preferable, and an aliphatic hydrocarbon group is more preferable.

The aliphatic hydrocarbon group may be a linear chain or a branched chain, and an alkyl group is preferable. Specifically, the same alkyl group as the alkyl group in $R^1$ described above is exemplified.

Furthermore, examples of the aromatic hydrocarbon group include an aryl group with 6 to 10 carbon atoms such as a phenyl group.

Furthermore, examples of the hydrocarbon group where the aliphatic hydrocarbon group and the aromatic hydrocarbon group are together linked include an aralkyl group with 7 to 10 carbon atoms such as a benzyl group.

Furthermore, when the organic group has an anionic group as a substituent, examples of the anionic group include $-SO_3^-$, $-COO^-$, and $-OPO_3^{2-}$, and $-SO_3^-$ is preferable.

On the other hand, when $R^9$ is an organic group with 1 to 10 carbon atoms which is not substituted with an anionic group, a counter ion may be bonded to the monovalent group represented by Formula (4-1).

The counter ion is not particularly limited as long as it is negatively charged, and examples thereof include halogeno ions such as a chlorine ion, a bromine ion, and an iodine ion; hydrogen sulfate ions; alkylsulfate ions such as a methylsulfate ion and an ethylsulfate ion; alkylsulfonate ions; arylsulfonate ions such as a dodecylbenzenesulfonate ion and a para-toluenesulfonate ion; alkenylsulfonate ions such as sodium 2-methyl-2-propene-1-sulfonic acid; and carboxylate ions such as an acetate ion.

The organic group with 1 to 10 carbon atoms represented by $R^{10}$ in Formula (4-2) described above has the same as the organic group with 1 to 10 carbon atoms represented by $R^1$ described above, and the divalent organic group with 1 to 8 carbon atoms represented by $R^{11}$ is the same as the divalent organic group with 1 to 8 carbon atoms represented by $R^7$ described above.

It should be noted that as X described above, the monovalent group represented by Formula (4-1) described above is preferable from the viewpoints of an effect for suppressing non-specific adsorption and peel resistance.

Furthermore, a total content of the repeating unit (A) in the whole repeating units is preferably 0.01 to 50% by mass, more preferably 0.1 to 20% by mass, further preferably 0.5 to 15% by mass, further preferably 1 to 10% by mass, and particularly preferably 1.5 to 5% by mass, from the viewpoints of an effect for suppressing non-specific adsorption, adsorptivity to a surface, peel resistance, and coatability.

It should be noted that the content of the repeating unit (A) can be measured by, for example, $^1$H-NMR, or $^{13}$C-NMR.

<Repeating Unit (B)>

The repeating unit (B) includes a group represented by the following Formula (2) in a side chain thereof.

 (2)

[In Formula (2), $R^3$ represents an alkanediyl group with 2 to 8 carbon atoms, $R^4$ represents a hydrogen atom or an organic group with 1 to 40 carbon atoms, and n has an average value of 1 or more.]

The number of carbon atoms of the alkanediyl group represented by $R^3$ in the above Formula (2) is preferably 2 to 4, more preferably 2 or 3, and further preferably 2. Furthermore, the alkanediyl group may be a linear chain or a branched chain, and preferred specific examples thereof include an ethane-1,1-diyl group and a propane-1,2-diyl group. It should be noted that when a plurality of $R^3$s are present, such n $R^3$s may be identical to or different from each other.

As the organic group represented by $R^4$ in Formula (2) described above, a hydrocarbon group is exemplified, an aliphatic hydrocarbon group, an aromatic hydrocarbon group, and a hydrocarbon group where they are linked are preferable, and an aliphatic hydrocarbon group is more preferable from the viewpoint of an effect for suppressing non-specific adsorption. The aliphatic hydrocarbon group may be a linear chain or a branched chain.

As the aliphatic hydrocarbon group, an alkyl group and an alkenyl group are preferable.

The number of carbon atoms of the alkyl group is preferably 1 to 25, more preferably 1 to 15, further preferably 1 to 10, further preferably 1 to 5, and particularly preferably 1 to 3. Specific examples of the alkyl group include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, an 2-ethyl-hexyl group, a dodecyl group, and a docosyl group.

Furthermore, the number of carbon atoms of the alkenyl group is preferably 2 to 25, more preferably 2 to 15, further preferably 2 to 10, further preferably 2 to 5, and particularly preferably 2 or 3. Specific examples of the alkenyl group include a vinyl group, a propenyl group, and a butenyl group or the like.

In terms of the number of carbon atoms of the aromatic hydrocarbon group, an aryl group is preferable.

The number of carbon atoms of the aryl group is preferably 6 to 20, more preferably 6 to 16, and further preferably 6 to 12. Specific examples of the aryl group include a phenyl group and a naphthyl group or the like.

Examples of the hydrocarbon group where the aliphatic hydrocarbon group and the aromatic hydrocarbon group are linked include an aralkyl group with 7 to 40 carbon atoms, an alkylaryl group with 7 to 40 carbon atoms, and an aralkylaryl group with 13 to 40 carbon atoms. Examples of the aralkyl group include a benzyl group or the like, and examples of the alkylaryl group include a nonylphenyl group or the like. Examples of the aralkylaryl group include 2,4,6-tris(1-phenylethyl)phenyl group or the like.

n in Formula (2) described above has an average value of 1 or more, and from the viewpoint of an effect for suppressing non-specific adsorption, has preferably an average value of 2 or more, more preferably an average value of 3 or more, further preferably an average value of 5 or more, and particularly preferably an average value of 7 or more, and has preferably an average value of 100 or less, more preferably an average value of 50 or less, further preferably an average value of 45 or less, further preferably an average value of 40 or less, further preferably an average value of 35 or less, further preferably an average value of 30 or less, and particularly preferably an average value of 25 or less.

It should be noted that the "average value" in the present specification can be measured by NMR.

Furthermore, preferred specific examples of the repeating unit (B) include those represented by the following Formula (5).

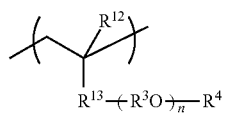

(5)

(6)

[In Formula (5), $R^{12}$ represents a hydrogen atom or a methyl group, $R^{13}$ represents —O—, —(C=O)—O—, —(C=O)—NR$^{14}$—, —NR$^{14}$—(C=O)— ($R^{14}$ represents a hydrogen atom or an organic group with 1 to 10 carbon atoms, and  denotes the position of bonding to the carbon atom to which $R^{12}$ is bonded in Formula (5)), or a phenylene group, and $R^3$, $R^4$, and n have the same meaning as described above.]

In Formula (5) described above, $R^{13}$ represents —O—, —(C=O)—O—, —(C=O)—NR$^{14}$—, **—NR$^{14}$—(C=O)—, or a phenylene group. Such a phenylene group is the same as the phenylene group represented by $R^6$. The organic group with 1 to 10 carbon atoms represented by $R^{14}$ is the same as the organic group with 1 to 10 carbon atoms represented by $R^8$.

Among such $R^{13}$s, from the viewpoints of an effect for suppressing non-specific adsorption and peel resistance, —O— and —(C=O)—O— are preferable, and —(C=O)—O— is more preferable.

Furthermore, from the viewpoints of an effect for suppressing non-specific adsorption, adsorptivity to a surface, peel resistance, and coatability, a total content of the repeating unit (B) in the whole repeating units is preferably 3% by mass or more, more preferably 30% by mass or more, further preferably 35% by mass or more, further preferably 40% by mass or more, further preferably 45% by mass or more, further preferably 50% by mass or more, further preferably 55% by mass or more, and further preferably 57% by mass or more. In a case where the polymer does not include the repeating unit (C), the total content of the repeating unit (B) is further preferably 80% by mass or more, further preferably 85% by mass or more, further preferably 90% by mass or more, and particularly preferably 95% by mass or more. Furthermore, from the same viewpoints as described above, the total content of the repeating unit (B) in the whole repeating units is preferably 99.99% by mass or less, more preferably 99.9% by mass or less, further preferably 99.5% by mass or less, further preferably 99% by mass or less, and particularly preferably 98.5% by mass or less.

It should be noted that the content of the repeating unit (B) may be measured in the same manner as in the content of the repeating unit (A).

A mass ratio of the repeating unit (B) to the repeating unit (A) included in the polymer, [(B)/(A)], is preferably 1 to 80, more preferably 5 to 80, further preferably 7.5 to 75, further preferably 10 to 75, further preferably 10 to 70, further preferably 10 to 65, and particularly preferably 13 to 65, from the viewpoints of an effect for suppressing non-specific adsorption, adsorptivity to a surface, peel resistance, and coatability.

<Repeating Unit (C)>

Furthermore, the polymer used in the present invention may further include a repeating unit including a group represented by the following Formula (6) (hereinafter, also referred to as the repeating unit (C)) in a side chain thereof for the purpose of controlling a hydrophilicity of the coated surface, in addition to the repeating units (A) and (B) described above.

[In Formula (6), $R^{15}$ and $R^{16}$ each independently represents a hydrogen atom or an organic group with 1 to 10 carbon atoms, and when both $R^{15}$ and $R^{16}$ are an organic group with 1 to 10 carbon atoms, $R^{15}$ and $R^{16}$ may together form a heterocyclic ring which may include a hetero atom other than a nitrogen atom.]

The number of carbon atoms of the organic groups represented by $R^{15}$ and $R^{16}$ in Formula (6) described above is preferably 1 to 6, more preferably 1 to 3, and further preferably 1 or 2.

Examples of the organic group include a hydrocarbon group and a group in which a part of the hydrogen atom of the hydrocarbon group is substituted with an alkanoyl group or an alkoxy group.

An aliphatic hydrocarbon group is preferable as the hydrocarbon group. The aliphatic hydrocarbon group may be a linear chain or a branched chain, and examples thereof include alkyl groups such as a methyl group, an ethyl group, an n-propyl group, an isopropyl group, an n-butyl group, an isobutyl group, a sec-butyl group, a tert-butyl group, a pentyl group, and a hexyl group.

Furthermore, as the alkanoyl group, an alkanoyl group with 2 to 6 carbon atoms is preferable, and an alkanoyl group with 2 to 4 carbon atoms is more preferable. The alkanoyl group may be a linear chain or a branched chain, and examples thereof include an acetyl group, a propionyl group, and a butyryl group.

Furthermore, examples of the group in which a part of the hydrogen atom of the hydrocarbon group is substituted with an alkanoyl group include a 1,1-dimethyl-2-acetylethyl group.

Furthermore, as the alkoxy group, an alkoxy group with 1 to 6 carbon atoms is preferable, and an alkoxy group with 1 to 4 carbon atoms is more preferable. The alkoxy group may be a linear chain or a branched chain, and examples thereof include a methoxy group, an ethoxy group, an n-propoxy group, an isopropoxy group, and an n-butoxy group.

Furthermore, examples of the group in which a part of the hydrogen atom of the hydrocarbon group is substituted with an alkoxy group include an n-butoxymethyl group.

Furthermore, as $R^{15}$ and $R^{16}$ in the Formula (6) described above, $R^{15}$ and $R^{16}$ which together form a heterocyclic ring which may include a hetero atom other than a nitrogen atom are preferable. In this case, as the hetero atom other than a nitrogen atom, for example, an oxygen atom is exemplified. Furthermore, examples of the heterocyclic ring include a piperidine ring and a morpholine ring or the like.

Furthermore, preferred specific examples of the repeating unit (C) include those represented by the following Formula (7).

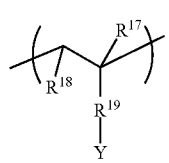

(7)

[In Formula (7), $R^{17}$ represents a hydrogen atom or a methyl group, $R^{18}$ represents a hydrogen atom or a dimethylaminomethyl group, $R^{19}$ represents —(C=O)—, —O—, *—(C=O)—O—, *—(C=O)—NR$^{20}$—, *—NR$^{20}$—(C=O)—($R^{20}$ represents a hydrogen atom or an organic group with 1 to 10 carbon atoms, and * denotes the position of bonding to the carbon atom to which $R^{17}$ is bonded in Formula (7)), or a divalent hydrocarbon group with 1 to 10 carbon atoms, and Y represents a monovalent group represented by the following Formula (8).

(8)

[In Formula (8), $R^{21}$ represents a single bond or a divalent hydrocarbon group with 1 to 6 carbon atoms, and $R^{15}$ and $R^{16}$ have the same meaning as described above.]]

In Formula (7), $R^{18}$ represents a hydrogen atom or a dimethylaminomethyl group, and a hydrogen atom is preferable.

In Formula (7), $R^{19}$ represents —(C=O)—, —O—, *—(C=O)—O—, *—(C=O)—NR$^{20}$—, ***—NR$^{20}$—(C=O)—, or a divalent hydrocarbon group with 1 to 10 carbon atoms. The organic group with 1 to 10 carbon atoms represented by $R^{20o}$ is the same as the organic group with 1 to 10 carbon atoms represented by $R^1$ described above.

Furthermore, as the divalent hydrocarbon group represented by $R^{19}$, a divalent aliphatic hydrocarbon group and a divalent aromatic hydrocarbon group are preferable, and an alkanediyl group and an arylene group are more preferable. The divalent aliphatic hydrocarbon group may be a linear chain or a branched chain.

The number of carbon atoms of the divalent aliphatic hydrocarbon group is preferably 1 to 4. Specific examples of the divalent aliphatic hydrocarbon group include the same alkanediyl group as the alkanediyl group in $R^7$ described above.

Furthermore, the number of carbon atoms of the divalent aromatic hydrocarbon group is preferably 6 to 10. Specific examples of the divalent aromatic hydrocarbon group include a phenylene group.

Among $R^{19}$s as described above, from the viewpoints of an effect for suppressing non-specific adsorption and peel resistance, —(C=O)— and a divalent hydrocarbon group are preferable, and —(C=O)— is more preferable.

In Formula (8), $R^{21}$ represents a single bond or a divalent hydrocarbon group with 1 to 6 carbon atoms, and the number of carbon atoms of such a divalent hydrocarbon group is preferably 1 to 3.

As the divalent hydrocarbon group, a divalent aliphatic hydrocarbon group is preferable. The divalent aliphatic hydrocarbon group may be a linear chain or a branched chain, and an alkanediyl group is preferable. Specific examples of the alkanediyl group include the same alkanediyl group as the alkanediyl group in $R^7$ described above.

Furthermore, among such $R^{21}$s, a single bond is preferable.

Furthermore, in a case where the polymer used in the present invention has the repeating unit (C), from the viewpoints of an effect for suppressing non-specific adsorption, adsorptivity to a surface, peel resistance, and coatability, a total content of the repeating unit (C) in the whole repeating unit is preferably 0.5% by mass or more, more preferably 1% by mass or more, further preferably 5% by mass or more, and particularly preferably 10% by mass or more, and is preferably 95% by mass or less, more preferably 90% by mass or less, further preferably 85% by mass or less, further preferably 80% by mass or less, further preferably 50% by mass or less, further preferably 45% by mass or less, further preferably 43% by mass or less, and particularly preferably 42% by mass or less.

The content of the repeating unit (C) may be measured in the same manner as in the content of the repeating unit (A).

Furthermore, in a case where the polymer used in the present invention has the repeating unit (C), a mass ratio of the repeating unit (C) to the repeating unit (A) included in the polymer, [(C)/(A)], is preferably 0.5 to 1000, more preferably 1 to 100, further preferably 3 to 50, further preferably 5 to 30, and particularly preferably 5 to 20, from the viewpoints of an effect for suppressing non-specific adsorption, adsorptivity to a surface, peel resistance, and coatability.

<Repeating Unit (D)>

The polymer used in the present invention may have a repeating unit (D) other than the repeating units (A) to (C) described above. Examples of such a repeating unit (D) include those derived from an anionic monomer, or a non-ionic monomer other than the monomers from which the repeating units (A) to (C) are derived, and one or two or more thereof may be included.

A monomer from which the repeating unit (D) is derived is not particularly limited, and one or more monomers selected from the group consisting of styrenes and (meth)acrylates are preferable.

Examples of the anionic monomer include unsaturated carboxylic acid monomers such as vinyl benzoate and (meth)acrylic acid; and unsaturated sulfonic acid monomers such as styrenesulfonic acid, 2-acrylamide-2-methylpropanesulfonic acid, and isoprenesulfonic acid.

Furthermore, as the nonionic monomer, specific examples of styrenes include styrene, 4-methylstyrene, 2,4-dimethylstyrene, 2,4,6-trimethylstyrene, 4-ethylstyrene, 4-isopropylstyrene, 4-tert-butylstyrene, and α-methylstyrene.

Furthermore, examples of the (meth)acrylates include $C_{1-10}$ alkyl(meth)acrylates such as methyl(meth)acrylate, ethyl(meth)acrylate, isobutyl(meth)acrylate, and 2-ethylhexyl (meth)acrylate; $C_{6-10}$ cycloalkyl(meth)acrylates such as cyclohexyl(meth)acrylate; and (meth)acrylate esters having a bridged cycle hydrocarbon group with 8 to 16 carbon atoms such as 1-adamantyl(meth)acrylate, 1-methyl-(1-adamantylethyl) (meth)acrylate, and tricyclo[5.2.1.0$^{2,6}$]decan-8-yl (meth)acrylate or the like. Furthermore, among these (meth)acrylates, a $C_{1-8}$ alkyl group is preferable as the $C_{1-10}$ alkyl group, a $C_{6-8}$ cycloalkyl group is preferable as the $C_{6-10}$ cycloalkyl group, and a bridged cycle hydrocarbon group with 8 to 12 carbon atoms is preferable as the bridged cycle hydrocarbon group with 8 to 16 carbon atoms.

Furthermore, as (meth)acrylates, a macromonomer having a (meth)acryloyloxy group at an end thereof, such as a polystyrene macromonomer having a (meth)acryloyloxy group at an end thereof, a polymethyl(meth)acrylate macromonomer having a (meth)acryloyloxy group at an end thereof (for example, Macromonomer AA-6 produced by TOAGOSEI CO., LTD.), a polybutyl(meth)acrylate macromonomer having a (meth)acryloyloxy group at an end thereof (for example, Macromonomer AB-6 produced by TOAGOSEI CO., LTD.), or a polydimethylsiloxane macromonomer having a (meth)acryloyloxy group at an end thereof (for example, modified silicone oil X-22-2475 produced by Shin-Etsu Chemical Co., Ltd.), may be used. When these macromonomers are used, a graft copolymer is obtained.

A total content of the repeating unit (D) in the whole repeating units is preferably 0 to 50% by mass, more preferably 0 to 40% by mass, further preferably 0 to 30% by mass, further preferably 0 to 20% by mass, further preferably 0 to 18% by mass, further preferably 0 to 10% by mass, and particularly preferably 0 to 1% by mass.

Furthermore, an embodiment of arrangement of the repeating units of the polymer used in the present invention is not particularly limited, and may be any of a block copolymer, a graft copolymer, a random copolymer, and an alternating copolymer.

Furthermore, the number average molecular weight ($M_n$) of the polymer used in the present invention is preferably 5000 to 500000, more preferably 10000 to 200000, and further preferably 10000 to 100000.

Furthermore, the weight average molecular weight ($M_w$) of the polymer used in the present invention is preferably 20000 to 2000000, more preferably 40000 to 800000, and further preferably 50000 to 400000.

Furthermore, the molecular weight distribution ($M_w/M_n$) is preferably 1 to 10 and more preferably 1 to 5.

It should be noted that the number average molecular weight, the weight average molecular weight, and the molecular weight distribution may be measured in accordance with a method described in Examples which will be described later.

Furthermore, the polymer used in the present invention is preferably water-soluble, from the viewpoint of an effect for suppressing non-specific adsorption. In the present specification, the term "water-soluble" used herein means that, when a polymer is added and mixed in water (25° C.) so that a polymer solid content is 1% by mass, the mixture becomes transparent visually.

The polymer used in the present invention can be synthesized by copolymerization of the monomer from which the repeating unit (A) is derived and the monomer from which the repeating unit (B) is derived, and as necessary, the monomer from which the repeating unit (C) or the repeating unit (D) is derived. The copolymerization may be carried out through an appropriate combination of common methods.

Examples of the monomer from which the repeating unit (A) is derived include a quaternary ammonium cation-containing cationic monomer and a quaternary ammonium cation-containing betaine monomer. These monomers may be used alone or in combination of two or more thereof.

Examples of the quaternary ammonium cation-containing cationic monomer include N,N-dimethylaminopropyl (meth)acrylamide methyl chloride-quaternary salt, N,N-dimethylaminoethyl (meth)acrylate methyl chloride-quaternary salt, (meth)acryloyloxyethyl dimethyl ethyl ammonium ethyl sulfate, (meth)acryloyloxyethyl dimethyl benzyl ammonium chloride, (meth)acryloyloxyethyl trimethyl ammonium chloride, (meth)acryloyloxyethyl trimethyl ammonium methyl sulfate, (meth)acryloyloxyethyl trimethyl ammonium p-toluene sulfonate, (meth)acryloylaminopropyl dimethyl ethyl ammonium ethyl sulfate, (meth)acryloylaminopropyl dimethyl benzyl ammonium chloride, (meth) acryloylaminopropyl trimethyl ammonium chloride, (meth)acryloylaminopropyl trimethyl ammonium methyl sulfate, (meth) acryloylaminopropyl trimethyl ammonium p-toluene sulfonate, and (vinylbenzyl)trimethyl ammonium chloride or the like.

Examples of the quaternary ammonium cation-containing betaine monomer include 2-(meth)acryloyloxyethyl phosphorylcholine, [3-((meth)acryloylamino)propyl]dimethyl(3-sulfopropyl)ammonium hydroxide, and [2-((meth)acryloyloxy)ethyl]dimethyl-(3-sulfopropyl)ammonium hydroxide or the like.

Examples of the monomer from which the repeating unit (B) is derived include (meth)acrylate-based monomers and vinyl ether-based monomers, and these monomers may be used alone or in combination of two or more thereof.

Examples of the (meth)acrylate-based monomers include (poly)ethylene glycol methyl ether(meth)acrylate, (poly)ethylene glycol ethyl ether(meth)acrylate, (poly)ethylene glycol butyl ether(meth)acrylate, (poly)ethylene glycol behenyl ether(meth)acrylate, octoxy (poly)ethylene glycol-(poly)propylene glycol mono(meth)acrylate, lauroxy(poly)ethylene glycol mono(meth)acrylate, (poly)ethylene glycol mono(meth)acrylate, (poly)propylene glycol mono(meth)acrylate, (poly) (ethylene glycol-propylene glycol) mono (meth)acrylate, (poly) (ethylene glycol-tetramethylene glycol) mono(meth)acrylate, (poly)(propylene glycol-tetramethylene glycol) mono(meth)acrylate, allyloxy (poly)ethylene glycol-(poly)propylene glycol mono(meth)acrylate, phenoxy(poly)ethylene glycol mono(meth)acrylate, nonylphenoxy(poly)ethylene glycol mono(meth)acrylate, nonylphenoxy (poly)ethylene glycol-(poly)propylene glycol mono(meth)acrylate, nonylphenoxy(poly)propylene glycol-(poly)ethylene glycol mono(meth)acrylate, (poly)ethylene glycol 2,4,6-tris(1-phenylethyl) phenyl ether (meth)acrylate, and 1-methoxyethyl(meth)acrylate.

Examples of the vinyl ether-based monomers include (poly)ethylene glycol vinyl ether or the like.

Examples of the monomer from which the repeating unit (C) is derived include primary amino group-containing monomers, secondary amino group-containing monomers, tertiary amino group-containing monomers, and amide group-containing monomers, and these monomers may be used alone or in combination of two or more thereof.

Examples of the primary amino group-containing monomers include allylamine hydrochloride, allylamine dihydrogenphosphate, 2-isopropenylaniline, 3-vinylaniline, and 4-vinylaniline or the like.

Examples of the secondary amino group-containing monomers include t-butylaminoethyl(meth)acrylate or the like.

Examples of the tertiary amino group-containing monomers include dimethylaminopropyl(meth)acrylamide, 2-(dimethylamino)ethyl (meth)acrylate, 3-(dimethylamino)propyl (meth)acrylate, 2-(diethylamino)ethyl (meth)acrylate, 2-(diisopropylamino)ethyl (meth)acrylate, 2-N-morpholinoethyl(meth)acrylate, N,N-dimethylvinylbenzylamine, and N,N,N',N'-tetramethyl-2-butene-1,4-diamine or the like.

Examples of the amide group-containing monomers include N-isopropyl(meth)acrylamide, N-(1,1-dimethyl-2-acetylethyl) (meth)acrylamide, N-n-butoxymethylacrylamide, hydroxyethyl(meth)acrylamide, (meth)acryloylpiperidine, and (meth)acryloylmorpholine or the like.

Furthermore, a content of the polymer in the surface treatment agent of the present invention is preferably 0.001 to 15% by mass, more preferably 0.01 to 10% by mass, and further preferably 0.05 to 1% by mass. Even in such a low concentration, an effect for suppressing non-specific adsorption with respect to a surface formed of an inorganic material is sufficiently obtained.

Furthermore, the surface treatment agent of the present invention may contain a solvent. Examples of the solvent include water; and alcohol-based solvents such as methanol, ethanol, and isopropyl alcohol, and these solvents may be used alone or in combination of two or more thereof. A content of such a solvent is not particularly limited, and is preferably 85 to 99.999%; by mass, more preferably 90 to 99.99% by mass, and further preferably 99 to 99.95% by mass.

Furthermore, the surface treatment agent of the present invention may contain, for example, a disinfectant, a preservative, a salt, or a buffer solution or the like, in addition to the polymer and the solvent.

As described in Examples hereinbelow, the surface treatment agent for a surface formed of an inorganic material of the present invention has an excellent effect for suppressing non-specific adsorption to a surface formed of an inorganic material, and also has excellent peel resistance. In addition, the surface treatment agent exhibits low cytotoxicity and has an effect for maintaining protein activity.

In the present specification, the non-specific adsorption suppression used herein means the suppression of non-specific adsorption or adhesion of a biological sample, such as protein, lipid, nucleic acid, or a cell, to a surface formed of an inorganic material.

The reason why the above-described effect for suppressing non-specific adsorption is exerted by the surface treatment agent of the present invention has not been clearly elucidated. However, it is expected that the suppression of adsorption or adhesion of the biological sample can be achieved by the following mechanism. Specifically, the polymer is adsorbed to a surface formed of an inorganic material of a tool or a device or the like due to the repeating unit (A), while a surface hydrophilic action and an excluded volume effect of the polymer are exerted due to the repeating unit (B). When the polymer having an electric charge like the repeating unit (A) is adsorbed to the surface, in many cases, the surface has generally the electric charge and the biological sample such as protein is likely to be adsorbed to the surface. However, when the repeating unit (A) is combined with the repeating unit (B), the non-specific adsorption of the biological sample to the surface to which the polymer is adsorbed is suppressed. That is, when the repeating unit (A) is combined with the repeating unit (B), it is possible to achieve the balance between contradictory performances, that is, the non-specific adsorption prevention and adsorption of the polymer to the inorganic material surface.

Thus, the surface treatment agent of the present invention can be widely used for clinical tests, diagnostic agents, or various studies, for example, and is particularly useful as, for example, a coating agent for a solid phase made of glass such as glass beads or a material made of glass (for example, a microarray substrate made of glass) among a clinical and diagnostic apparatus, and a cell culture base material; and an antifouling agent, a cleaning agent, or a rinse agent or the like for assay cells of an automated analyzer used in diagnosis such as a blood test.

Furthermore, examples of the inorganic material include glass materials such oxide glass (for example, borosilicate glass having silicon dioxide as a main component), chalcogenide, inorganic glass (for example, halide), metal alloy glass, and quartz; metal materials such as gold, silver, copper, stainless steel, Ni—Ti alloys, Cu—Al—Mn alloys, tantalum, Co—Cr alloys, iridium, iridium oxide, niobium, silicon, aluminum, tantalum, titanium, and iron; metal oxides such as silicon dioxide, aluminum oxide, titanium oxide, and silver oxide; metal nitrides such as silicon nitride and aluminum nitride; ceramic materials such as oxide-based ceramic, nitride-based ceramic, carbide-based ceramic, silicide-based ceramic, and boride-based ceramic; cement materials; or inorganic materials having these materials as main components. In particular, the polymer used in the present invention is suitable for a surface treatment agent for glass.

It should be noted that examples of the above-described cells include anchorage-dependent cells and suspension cells (for example, blood cells such as leucocytes, erythrocytes, and platelets). Examples of the anchorage-dependent cells include cancer cells such as HeLa cells and F9 cells; fibroblasts such as 3T3 cells; stem cells such as ES cells, iPS cells, and mesenchymal stem cells; renal cells such as HEK293 cells; neuronal cells such as NT2 cells; endothelial cells such as UVf2 (f: female) cells and HMEC-1 cells; myocardial cells such as H9c2 cells; and epithelial cells such as Caco-2 cells.

Furthermore, it is possible to obtain a base material having a modified surface, the base material including the polymer having the repeating units (A) and (B) described above on at least a part of the surface formed of an inorganic material, by bringing the base material having a surface formed of an inorganic material into contact with the surface treatment agent.

Here, the base material having a modified surface may be obtained in the same manner as a general method for coating the base material with the surface treatment agent. Specific examples of the method include: (1) a method for bringing a surface treatment agent solution into contact with a base material, and physically adsorbing the polymer used in the present invention to the surface of the base material in the solution, with the solvent remaining; and (2) a method for bringing a surface treatment agent solution into contact with a base material, and evaporating the solvent through drying, to thereby form a dry film of the polymer used in the present invention on the surface of the base material.

In the above method (1), after physical adsorption of the polymer used in the present invention to the surface of the base material in the solution, generally, the solvent is removed by tilting the base material to cause the solution to flow out, by pulling the base material from the solution, by blowing off the solution remaining on the base material, or by adding a large amount of solvent or the like, thereby obtaining a base material to which the polymer used in the present invention has been adsorbed. In the present invention, the method (1) is preferable from the viewpoint that the load to the environment is low, and the polymer used in the present invention is not eluted off during the use of the treated base material.

As the base material having a modified surface as described above, a tool and a device having a modified surface are exemplified.

[Tool and Device Having Modified Surface]

The tool and the device having a modified surface of the present invention have the polymer having the repeating units (A) and (B) described above on at least a part of the surface formed of an inorganic material (for example, the tool and the device are coated with the polymer). Specifically, a surface (which may be any of an inner wall surface or an outer wall surface) of the tool or the device is modified by applying the polymer onto at least a part of the surface so that a non-specific adsorption prevention layer is formed on the surface thereof. As the inorganic material forming the surfaces of the tool and the device, the same inorganic material as described above is exemplified. Furthermore, as the tool and the device, a tool and a device for medical application or culturing are preferable.

Furthermore, the tool to be modified may be a tool in which at least a part of the surface is formed of an inorganic material, and examples thereof include beads, microarray substrates, microplates, and cells or the like.

Furthermore, the device to be modified may be a device in which at least a part of the surface is formed of an inorganic material, and examples thereof include medical devices (a clinical and diagnostic apparatus, a biosensor, a cardiac pacemaker, an implantation-type bio-chip), fermentation units, and bioreactors or the like.

Furthermore, the tool and the device having a modified surface of the present invention can be produced by the method including a step of coating at least a part of the surface formed of an inorganic material with a polymer having the repeating units (A) and (B) described above.

Specifically, the polymer and the tool or the device are prepared, and the polymer may be applied onto at least a part of the tool or the device (preferably, a portion where the tool or the device and protein come into contact with each other when the tool or the device is used). In such application, a polymer solution including the polymer (a surface treatment agent) may be brought into contact with a portion to be desired to be coated.

The contact time is generally 1 second to 48 hours, and preferably 15 seconds to 24 hours. Furthermore, the contact temperature is generally 0 to 50° C., and may be room temperature (25° C.). It should be noted that the polymer may be cured by using a cross-linking agent or a crosslinkable monomer. Furthermore, the polymer may be chemically bonded to a surface of the inorganic material by using a cross-linking agent or a crosslinkable monomer.

Furthermore, after the surface treatment agent of the present invention is brought into contact with the tool or the device, removal of a solvent and drying may be performed as necessary. The removing and drying means may be carried out through an appropriate combination of processes of, for example, evaporating the solvent through drying, tilting the tool or the device to cause the solution to flow out, pulling the tool or the device from the solution, blowing off the solution remaining on the tool or the device, or adding a large amount of solvent or the like. According to this, a dry film of the surface treatment agent of the present invention is formed on the surface of the tool or the device.

It should be noted that the tool and the device can also be produced by a method for producing a tool or a device by using an inorganic material in such a manner that the inorganic material is coated with the surface treatment agent of the present invention by the same method as described above.

Furthermore, as an example of the tool or the device, a biomedical structure and a microchannel device are exemplified.

<Biomedical Structure>

The biomedical structure has the polymer having the repeating units (A) and (B) described above on at least a part of the surface formed of an inorganic material.

The term "biomedical structure" used herein refers to a medical structure used in a living body, and such structures are classified roughly into a structure which is implanted in a body, and a structure which is used in a body. It should be noted that the size or length of the biomedical structure is not particularly limited, and the biomedical structure encompasses a structure having a microcircuit, and a structure for detecting a trace amount of a sample. It should be noted that regarding the coating, the polymer may be applied to the structure through film coating in addition to adsorption. Alternatively, the adsorbed polymer may be made water-insoluble through cross linking or the polymer may be chemically bonded to the surface of material, to thereby impart durability to the structure.

Examples of the structure which is implanted in a body for use include a device for assisting the function of a living body suffering from a disease, such as a cardiac pacemaker; a device for detecting abnormality in a living body, such as an implantation-type bio-chip; and medical tools such as an implant, a bone fixation material, a surgical suture, and an artificial blood vessel.

Furthermore, examples of the structure which is used in a body include a catheter, a gastroscope, a microfiber, and a nanofiber, in addition to drug delivery vehicles such as vesicles, microparticles, and nanoparticles.

Furthermore, the coating of the polymer may be carried out in such a manner that the polymer is optionally mixed with a solvent that is used in a surface treatment agent, and the resultant mixture is applied onto at least a part of the surface (including the inner wall and the outer wall) of the structure through a known method. Specific examples of the method include a spray coating method, a dip coating method, a flow coating method, brushing, and sponge coating. In addition, coating can be carried out only by immersing the surface of the structure in the polymer solution, thereby bringing the structure into contact with the polymer.

The application of the polymer is preferably carried out at a portion where the biomedical structure and the biological tissue come into contact with each other in a body.

<Microchannel Device>

The microchannel device of the present invention includes a microchannel having the polymer having the repeating units (A) and (B) described above on at least a part of the surface formed of an inorganic material.

Examples of the microchannel device include microreaction devices (specifically, for example, a microreactor and a microplant); microanalysis devices such as an integrated nucleic acid analysis device, micro electrophoresis device, and a micro chromatography device; micro devices for preparation of samples for analysis such as a mass spectrometry and a liquid chromatography; physicochemical treatment devices used for, for example, extraction, membrane separation, and dialysis; microchannel chips such as an environmental analysis chip, a clinical analysis chip, a gene analysis chip (DNA chip), a protein analysis chip (proteome chip), a sugar-chain chip, a chromatographic chip, a cell analysis chip, and a drug screening chip.

Furthermore, the microchannel provided in the above-described device is a portion through which a trace amount of a sample (preferably a liquid sample) flows, and the channel width and depth thereof are not particularly limited. Each of the channel width and the depth is generally about 0.1 µm to 1 mm, and preferably 10 µm to 800 µm.

It should be noted that the channel width and the depth of the microchannel may be the same over the entire channel length. Alternatively, different portions of the microchannel may have different sizes or shapes.

It should be noted that the coating of the polymer may be carried out in the same manner as the coating of the polymer to the biomedical structure. The coating is preferably carried out on almost the entire surface (including the entire surface) of the channel.

EXAMPLES

Hereinafter, the present invention will be described in detail by Examples, and the present invention is not limited to these Examples.

Each analysis condition in Examples is as follows.

<Molecular Weight Measurement (Elution Solvent: Water-Ethanol Mixed Solvent)>

The weight average molecular weight (Mw) and the number average molecular weight (Mn) were measured through gel permeation chromatography (GPC) using polyethyleneglycol as a standard by use of TSKgel G6000PWXL-CP column manufactured by Tosoh Corporation under the analysis conditions of a flow rate: 0.3 mL/min, an elution solvent: water-ethanol mixed solvent ($NaNO_3$: 0.1 M, ethanol: 20(v/v)%), and a column temperature: 25° C.

<$^1$H-NMR Spectra>

$^1$H-NMR spectra were measured by means of AVANCE 500 (500 MHz) (product model manufactured by Bruker Corporation) using $D_2O$ as a solvent and sodium 3-(trimethylsilyl)-2,2',3,3'-tetradeuteropropionnate (TMSP-d4) as an internal standard material.

<$^{13}$C-NMR Spectra>

$^{13}$C-NMR spectra were measured by means of AVANCE 500 (500 MHz) (product model manufactured by Bruker Corporation) using $D_2O$ as a solvent and sodium 3-(trimethylsilyl)-2,2',3,3'-tetradeuteropropionate (TMSP-d4) as an internal standard material.

<Absorbance Measurement>

Regarding absorbance, the absorbance was measured at 450 nm by means of 680 microplate reader (product model manufactured by Nippon Bio-Rad Laboratories Inc.).

Example 1

Synthesis of Copolymer (N-1-1)

A copolymer (N-1-1) was obtained according to the following synthesis route.

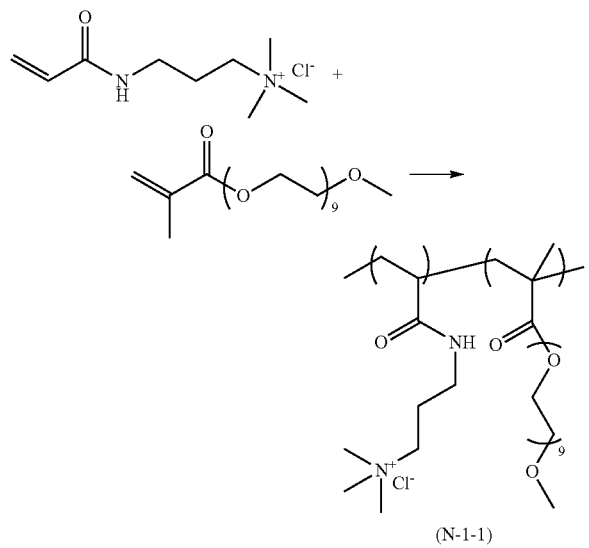

(N-1-1)

4.00 g of aqueous solution of 75% N,N-dimethylaminopropylacrylamide methyl chloride-quaternary salt (produced by KOHJIN Film & Chemicals Co., Ltd.; hereinafter, referred to as DMAPAA-Q), 47.0 g of methoxypolyethyleneglycol methacrylate (M-90G (including nine oxyethylene units per molecule on average) produced by Shin Nakamura Chemical Co., Ltd.; hereinafter, referred to as MPEGM), 2.00 g of 2,2'-azobis[2-(2-imidazolin-2-yl)propane]dihydrochloride as a polymerization initiator, 0.250 g of 2-aminoethanethiol hydrochloride as a chain-transfer agent, and 992 g of ion-exchange water were mixed together and transferred to a flask. While nitrogen was blown in the flask, the mixture was heated to 60° C. and allowed to polymerize for 6 hours, and then the reaction mixture was cooled to room temperature. The aqueous solution thus obtained was dialyzed, thereby obtaining the copolymer (N-1-1) (yield: 74%).

The molecular weight of the obtained copolymer (N-1-1) was measured using a water-ethanol mixed solvent as an eluate, and as a result, the number average molecular weight was 29000 and the molecular weight distribution was 3.3.

Furthermore, the structure of the copolymer (N-1-1) and the DMAPAA-Q/MPEGM ratio were confirmed by $^1$H-NMR. In the copolymer (N-1-1), the content of the repeating unit derived from DMAPAA-Q was 2.4% by mass and the content of the repeating unit derived from MPEGM was 97.6% by mass.

It should be noted that when the copolymer (N-1-1) was mixed with water so as to adjust the concentration to 1% by mass, the copolymer (N-1-1) was in a dissolution state in water.

Example 2

Synthesis of Copolymer (N-1-2)

A copolymer (N-1-2) was obtained in accordance with the same synthesis route as in Example 1 described above.

That is, 0.133 g of aqueous solution of 75% DMAPAA-Q, 9.90 g of MPEGM, 0.400 g of 2,2'-azobis[2-(2-imidazolin-2-yl)propane]dihydrochloride as a polymerization initiator, 0.0100 g of 2-aminoethanethiol hydrochloride as a chain-transfer agent, and 93.7 g of ion-exchange water were mixed together and transferred to a flask. While nitrogen was blown in the flask, the mixture was heated to 60° C. and allowed to polymerize for 3 hours, and then the reaction mixture was cooled to room temperature. The aqueous solution thus obtained was dialyzed, thereby obtaining the copolymer (N-1-2) (yield: 83%).

The molecular weight of the obtained copolymer (N-1-2) was measured using a water-ethanol mixed solvent as an eluate, and as a result, the number average molecular weight was 33000 and the molecular weight distribution was 3.7.

Furthermore, the structure of the copolymer (N-1-2) and the DMAPAA-Q/MPEGM ratio were confirmed by $^1$H-NMR. In the copolymer (N-1-2), the content of the repeating unit derived from DMAPAA-Q was 1.6% by mass and the content of the repeating unit derived from MPEGM was 98.4% by mass.

It should be noted that when the copolymer (N-1-2) was mixed with water so as to adjust the concentration to 1% by mass, the copolymer (N-1-2) was in a dissolution state in water.

Example 3

Synthesis of Copolymer (N-1-3)

A copolymer (N-1-3) was obtained in accordance with the same synthesis route as in Example 1 described above.

That is, 0.400 g of aqueous solution of 75% DMAPAA-Q, 4.70 g of MPEGM, 0.200 g of 2,2'-azobis[2-(2-imidazolin-2-yl)propane]dihydrochloride as a polymerization initiator, 0.0250 g of 2-aminoethanethiol hydrochloride as a chain-transfer agent, and 99.2 g of ion-exchange water were mixed together and transferred to a flask. While nitrogen was blown in the flask, the mixture was heated to 60° C. and allowed to polymerize for 3 hours, and then the reaction mixture was cooled to room temperature. The aqueous solution thus obtained was dialyzed, thereby obtaining the copolymer (N-1-3) (yield: 62%).

The molecular weight of the obtained copolymer (N-1-3) was measured using a water-ethanol mixed solvent as an eluate, and as a result, the number average molecular weight was 27000 and the molecular weight distribution was 3.3.

Furthermore, the structure of the copolymer (N-1-3) and the DMAPAA-Q/MPEGM ratio were confirmed by $^1$H-NMR. In the copolymer (N-1-3), the content of the repeating unit derived from DMAPAA-Q was 2.1% by mass and the content of the repeating unit derived from MPEGM was 97.9% by mass.

It should be noted that when the copolymer (N-1-3) was mixed with water so as to adjust the concentration to 1% by mass, the copolymer (N-1-3) was in a dissolution state in water.

Example 4

Synthesis of Copolymer (N-1-4)

A copolymer (N-1-4) was obtained in accordance with the same synthesis route as in Example 1 described above.

That is, 1.20 g of aqueous solution of 75% DMAPAA-Q, 9.10 g of MPEGM, 0.400 g of 2,2'-azobis[2-(2-imidazolin-2-yl)propane]dihydrochloride as a polymerization initiator, 0.0100 g of 2-aminoethanethiol hydrochloride as a chain-transfer agent, and 93.4 g of ion-exchange water were mixed together and transferred to a flask. While nitrogen was blown in the flask, the mixture was heated to 60° C. and allowed to polymerize for 3 hours, and then the reaction mixture was cooled to room temperature. The aqueous solution thus obtained was dialyzed, thereby obtaining the copolymer (N-1-4) (yield: 77%).

The molecular weight of the obtained copolymer (N-1-4) was measured using a water-ethanol mixed solvent as an eluate, and as a result, the number average molecular weight was 40000 and the molecular weight distribution was 3.3.

Furthermore, the structure of the copolymer (N-1-4) and the DMAPAA-Q/MPEGM ratio were confirmed by $^1$H-NMR. In the copolymer (N-1-4), the content of the repeating unit derived from DMAPAA-Q was 5.1% by mass and the content of the repeating unit derived from MPEGM was 94.9% by mass.

It should be noted that when the copolymer (N-1-4) was mixed with water so as to adjust the concentration to 1% by mass, the copolymer (N-1-4) was in a dissolution state in water.

Example 5

Synthesis of Copolymer (N-1-5)

A copolymer (N-1-5) was obtained in accordance with the following synthesis route.

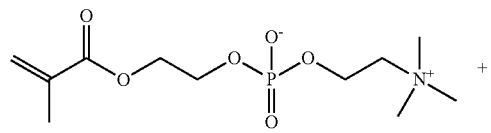

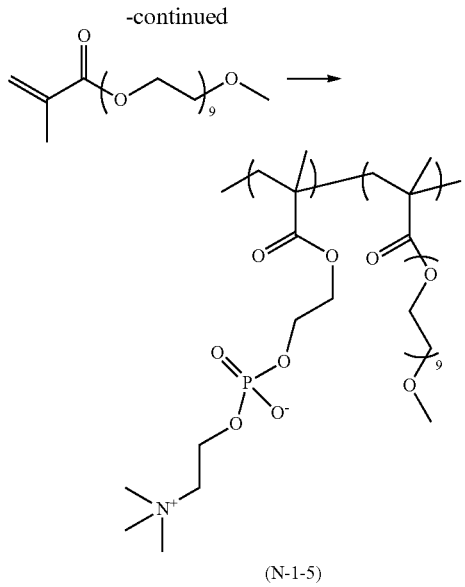

(N-1-5)

0.300 g of 2-methacryloyloxyethyl phosphorylcholine (produced by Tokyo Chemical Industry Co., Ltd.; hereinafter, referred to as MPC), 4.70 g of MPEGM, 0.200 g of 2,2'-azobis[2-(2-imidazolin-2-yl)propane]dihydrochloride as a polymerization initiator, 0.0250 g of 2-aminoethanethiol hydrochloride as a chain-transfer agent, and 99.3 g of ion-exchange water were mixed together and transferred to a flask. While nitrogen was blown in the flask, the mixture was heated to 60° C. and allowed to polymerize for 6 hours, and then the reaction mixture was cooled to room temperature. The aqueous solution thus obtained was dialyzed, thereby obtaining the copolymer (N-1-5) (yield: 64%).

The molecular weight of the obtained copolymer (N-1-5) was measured using a water-ethanol mixed solvent as an eluate, and as a result, the number average molecular weight was 25000 and the molecular weight distribution was 4.3.

Furthermore, the structure of the copolymer (N-1-5) and the MPC/MPEGM ratio were confirmed by $^1$H-NMR. In the copolymer (N-1-5), the content of the repeating unit derived from MPC was 9.6% by mass and the content of the repeating unit derived from MPEGM was 90.4% by mass.

It should be noted that when the copolymer (N-1-5) was mixed with water so as to adjust the concentration to 1% by mass, the copolymer (N-1-5) was in a dissolution state in water.

Example 6

Synthesis of Copolymer (N-1-6)

A copolymer (N-1-6) was obtained in accordance with the following synthesis route.

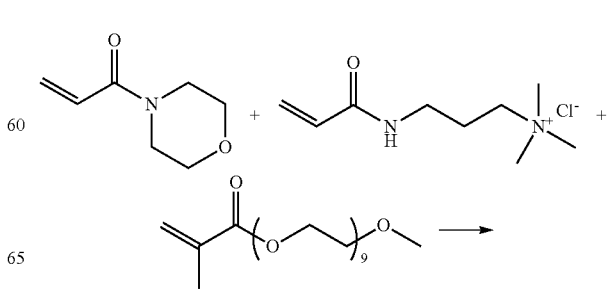

-continued

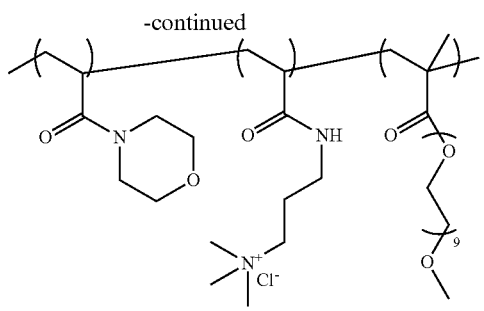

1.00 g of acryloylmorpholine (produced by KOHJIN Film & Chemicals Co., Ltd.; hereinafter, referred to as ACMO), 0.200 g of aqueous solution of 75% DMAPAA-Q, 1.35 g of MPEGM, 0.100 g of 2,2'-azobis[2-(2-imidazolin-2-yl)propane]dihydrochloride as a polymerization initiator, 0.0130 g of 2-aminoethanethiol hydrochloride as a chain-transfer agent, and 49.6 g of ion-exchange water were mixed together and transferred to a flask. While nitrogen was blown in the flask, the mixture was heated to 60° C. and allowed to polymerize for 6 hours, and then the reaction mixture was cooled to room temperature. The aqueous solution thus obtained was dialyzed, thereby obtaining the copolymer (N-1-6) (yield: 79%).

The molecular weight of the obtained copolymer (N-1-6) was measured using a water-ethanol mixed solvent as an eluate, and as a result, the number average molecular weight was 52000 and the molecular weight distribution was 2.6.

Furthermore, the structure of the copolymer (N-1-6) was confirmed by $^1$H-NMR and the ACMO/DMAPAA-Q/MPEGM ratio was confirmed by $^{13}$C-NMR. In the copolymer (N-1-6), the content of the repeating unit derived from ACMO was 37.9% by mass, the content of the repeating unit derived from DMAPAA-Q was 4.6% by mass, and the content of the repeating unit derived from MPEGM was 57.5% by mass.

It should be noted that when the copolymer (N-1-6) was mixed with water so as to adjust the concentration to 1% by mass, the copolymer (N-1-6) was in a dissolution state in water.

Test Example 1

Measurement of Amount of Adsorbed Antibody

A 96-well microplate made of glass (manufactured by Nippon Sheet Glass Co., Ltd.) was filled with each of 0.1% by mass of aqueous solution of the copolymer (N-1-1) (Example 7), blocking reagent N101 for immunoassay (produced by NOF CORPORATION) diluted 5-fold with ultrapure water (Comparative Example 1), and blocking reagent N102 for immunoassay (produced by NOF CORPORATION) diluted 5-fold with ultrapure water (Comparative Example 2), and incubated at room temperature for 5 minutes, followed by washing four times with ultrapure water.

Subsequently, the microplate was filled with an aqueous solution of a horseradish peroxidase-labeled mouse IgG antibody (AP124P: produced by Merck Millipore Corporation), and incubated at room temperature for 1 hour, followed by washing four times with PBS buffer. Then, color development was carried out by means of TMB (3,3',5,5'-tetramethylbenzidine)/hydrogen peroxide/sulfuric acid, and the absorbance was measured at 450 nm. The amount of adsorbed antibody was calculated from this absorbance by a calibration curve method.

Furthermore, for control, the amount of adsorbed antibody was calculated in the same manner as described above, except that the plate was not treated with the copolymer aqueous solution.

It should be noted that N101 and N102 correspond to a copolymer aqueous solutions of MPC with n-butyl methacrylate (n-BMA).

The results of Test Example 1 are shown in Table 1.

|  | Amount of adsorbed antibody (ng) |
|---|---|
| Control | 3.36 |
| Example 7 | 0 (detection limit or less) |
| Comparative Example 1 | 0.13 |
| Comparative Example 2 | 0.09 |

As shown in the above Table 1, the copolymer (N-1-1) has an excellent effect for suppressing non-specific adsorption with respect to glass.

Test Example 2

Peel Resistance Test (1)

(1) A glass cell (manufactured by SEKIYARIKA Co., Ltd.) was filled with 0.1% by mass of aqueous solution of the copolymer (N-1-1), and incubated at room temperature for 15 seconds, followed by washing twice with ultrapure water.

(2) Subsequently, the glass cell was filled with each of 1% by mass aqueous solutions of surfactants shown in the following Table 2 (Examples 8 to 17), and incubated at 37° C. for 1 hour, followed by washing four times with ultrapure water.

(3) Thereafter, the glass cell was filled with 2 mg/mL of aqueous solution of a human IgG polyclonal antibody, and incubated at 37° C. for 15 minutes, followed by washing four times with ultrapure water. Then, the amount of adsorbed antibody to the cell surface was quantitated using Micro BCA Protein Assay Reagent Kit (#23235: manufactured by Thermo Fisher Scientific K.K.) in terms of albumin.

Furthermore, for control, the amount of adsorbed antibody to the cell surface was measured by performing only the (3) adsorption treatment without performing the (1) copolymer aqueous solution treatment and the (2) surfactant aqueous solution treatment.

Moreover, for Example 18, the amount of adsorbed antibody to the cell surface was measured by performing only the (1) copolymer aqueous solution treatment and the (3) adsorption treatment without performing the (2) surfactant aqueous solution treatment.

The results of Test Example 2 are shown in Table 2.

|  | Copolymer aqueous solution treatment | Surfactant | Amount of adsorbed antibody (µg) |
|---|---|---|---|
| Control | Not Performed | — | 3.06 |
| Example 8 | Performed | Triton X-100 (produced by Sigma-Aldrich Co. LLC.) | 0.11 |

-continued

| | Copolymer aqueous solution treatment | Surfactant | Amount of adsorbed antibody (μg) |
|---|---|---|---|
| Example 9 | Performed | EMULGEN 1135S-70 (produced by Kao Corporation) | 0.16 |
| Example 10 | Performed | EMULGEN 123P (produced by Kao Corporation) | 0.15 |
| Example 11 | Performed | ADEKA TOL SO-135 (produced by ADEKA CORPORATION) | 0.08 |
| Example 12 | Performed | ADEKA NOL NK-4 (produced by ADEKA CORPORATION) | 0.11 |
| Example 13 | Performed | Nikkol BL9-EX (produced by Nikko Chemicals Co., Ltd.) | 0.09 |
| Example 14 | Performed | NOIGEN EA-177 (produced by DKS Co. Ltd.) | 0.09 |
| Example 15 | Performed | NEODOL 23-6.8 (produced by Shell Chemicals) | 0.06 |
| Example 16 | Performed | Tween 20 (produced by Sigma-Aldrich Co. LLC.) | 0.09 |
| Example 17 | Performed | Tween 80 (produced by Sigma-Aldrich Co. LLC.) | 0.18 |
| Example 18 | Performed | — | 0.05 |

As shown in the above Table 2, if glass is treated with the copolymer (N-1-1), the non-specific adsorption with respect to glass is less likely to occur even when the glass is treated with various surfactants after the treatment with the copolymer (N-1-1).

From this result, it found that the copolymer (N-1-1) has excellent peel resistance.

Test Example 3

Measurement of Amount of Adsorbed Bovine Serum Albumin (Hereinafter, Referred to as BSA)

A glass cell (manufactured by SEKIYARIKA Co., Ltd.) was filled with each of 0.1% by mass of aqueous solutions of the copolymer (N-1-2) to the copolymer (N-1-5) (Examples 19 to 22), and incubated at room temperature for 15 seconds, followed by washing twice with ultrapure water.

Thereafter, the glass cell was filled with 2mg/mL of aqueous solution of BSA (produced by Sigma-Aldrich Co. LLC.), and incubated at 37° C. for 18 hours, followed by washing four times with ultrapure water. Then, the amount of adsorbed BSA to the cell surface was quantitated using Micro BCA Protein Assay Reagent Kit (#23235: manufactured by Thermo Fisher Scientific K.K.).

Subsequently, for control, the amount of adsorbed BSA to the cell surface was measured in the same manner as described above, except that the cell was not treated with the aqueous solutions of the copolymer (N-1-2) to the copolymer (N-1-5), and the effect for suppressing non-specific adsorption was evaluated from a numerical value calculated by dividing the BSA amount in the case of using each copolymer aqueous solution described above by this value of the amount of adsorbed BSA.

The results of Test Example 3 are shown in Table 3.

| | Copolymer | Amount of adsorbed BSA (times) |
|---|---|---|
| Control | — | 1 |
| Example 19 | (N-1-2) | 0.345 |
| Example 20 | (N-1-3) | 0.356 |
| Example 21 | (N-1-4) | 0.908 |
| Example 22 | (N-1-5) | 0.632 |

As shown in the above Table 3, the copolymer (N-1-2) to the copolymer (N-1-5) have an excellent effect for suppressing non-specific adsorption with respect to glass.

Test Example 4

Peel Resistance Test (2)

(1) The copolymer (N-1-6) was dissolved in a 0.01 M NaCl aqueous solution such that the concentration became 0.1% by mass (Example 23), and a glass cell (manufactured by SEKIYARIKA Co., Ltd.) was filled with the obtained solution, and incubated at room temperature for 15 seconds, followed by washing twice with ultrapure water.

(2) Subsequently, the glass cell was filled with a 0.1 M NaCl aqueous solution, and incubated at 37° C. for 1 hour, followed by washing four times with ultrapure water.

(3) Thereafter, the glass cell was filled with 2 mg/mL of aqueous solution of a human IgG polyclonal antibody, and incubated at 37° C. for 15 minutes, followed by washing four times with ultrapure water. Then, the amount of adsorbed antibody to the cell surface was quantitated using Micro BCA Protein Assay Reagent Kit (#23235: manufactured by Thermo Fisher Scientific K.K.) in terms of albumin.

Furthermore, for control, the amount of adsorbed antibody to the cell surface was measured by performing only the (3) adsorption treatment without performing the (1) copolymer solution treatment and the (2) NaCl aqueous solution treatment.

Moreover, for Example 24, the amount of adsorbed antibody to the cell surface was measured by performing only the (1) copolymer solution treatment and the (3) adsorption treatment without performing the (2) NaCl aqueous solution treatment.

The results of Test Example 4 are shown in Table 4.

| | Copolymer solution treatment | NaCl aqueous solution treatment | Amount of adsorbed antibody (μg) |
|---|---|---|---|
| Control | Not Performed | Not Performed | 3.23 |
| Example 23 | Performed | Performed | 0.05 |
| Example 24 | Performed | Not Performed | 0.03 |

As shown in the above Table 4, it glass is treated with the copolymer (N-1-6), the non-specific adsorption with respect to glass is less likely to occur even when the glass is treated with a salt after the treatment with the copolymer (N-1-6).

From this result, it found that the copolymer (N-1-6) has excellent peel resistance.

The invention claimed is:

1. A tool, comprising:
a surface formed of an inorganic material, and
a non-crosslinked polymer comprising a repeating unit (A) and a repeating unit (B) physically adsorbed directly on at least a part of the surface formed of an inorganic material, wherein the repeating unit (A) is represented by Formula (3):

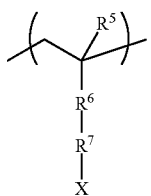

(3)

where $R^5$ represents a hydrogen atom or a methyl group, $R^6$ represents —O—, *—(C=O)—O—, *—(C=O)—NR$^8$—, *—NR$^8$—(C=O)—($R^8$ represents a hydrogen atom or an organic group with 1 to 10 carbon atoms, and * denotes the position of bonding to the carbon atom to which $R^5$ is bonded in Formula (3)), or a phenylene group, $R^7$ represents a divalent organic group with 1 to 8 carbon atoms, and X represents a monovalent group represented by Formula (4-1):

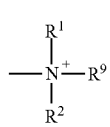

(4-1)

where $R^1$ and $R^2$ each independently represents a hydrocarbon group comprising 1 to 10 carbon atoms, and $R^9$ represents a hydrocarbon group with 1 to 10 carbon atoms, and the repeating unit (B) comprises a group represented by Formula (2) in a side chain thereof

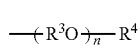

(2)

where $R^3$ represents an alkanediyl group comprising 2 to 8 carbon atoms, $R^4$ represents a hydrogen atom or an organic group comprising 1 to 40 carbon atoms, and n has an average value of 1 or more.

2. A modified glass surface, comprising:
a surface formed of oxide glass, chalcogenide, inorganic glass, metal alloy glass, or quartz, and
a non-crosslinked polymer directly physically adsorbed to at least a part of said surface formed of oxide glass, chalcogenide, inorganic glass, metal alloy glass, or quartz, wherein
the non-crosslinked polymer comprises a repeating unit (A) and a repeating unit (B), the repeating unit (A) is represented by Formula (3):

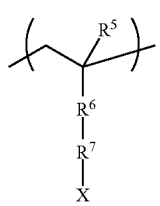

(3)

where $R^5$ represents a hydrogen atom or a methyl group, $R^6$ represents —O—, *—(C=O)—O—, *—(C=O)—NR$^8$—, *—NR$^8$—(C=O)— where $R^8$ represents a hydrogen atom or an organic group with 1 to 10 carbon atoms, and * denotes the position of bonding to the carbon atom to which $R^5$ is bonded in Formula (3), or a phenylene group, $R^7$ represents a divalent organic group with 1 to 8 carbon atoms, and X represents a monovalent group represented by Formula (4-1):

(4-1)

—N$^+$—R$^9$ where $R^1$ and $R^2$ each independently represents a hydrocarbon group comprising 1 to 10 carbon atoms, and $R^9$ represents a hydrocarbon group with 1 to 10 carbon atoms, and the repeating unit (B) comprises a group represented by Formula (2) in a side chain thereof —(R$^3$O)$_n$—R$^4$ (2)

where $R^3$ represents an alkanediyl group comprising 2 to 8 carbon atoms, $R^4$ represents a hydrogen atom or an organic group comprising 1 to 40 carbon atoms, and n has an average value of 1 or more.

3. A method for treating a surface formed of an inorganic material, the method comprising:
physically adsorbing a non-crosslinked polymer directly to at least a part of said surface formed of an inorganic material, wherein
the non-crosslinked polymer comprises a repeating unit (A) and a repeating unit (B), the repeating unit (A) is represented by Formula (3):

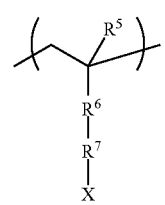

(3)

where $R^5$ represents a hydrogen atom or a methyl group, $R^6$ represents —O—, *—(C=O)—O—, *—(C=O)—NR$^8$—, *—NR$^8$—(C=O)— where $R^8$ represents a hydrogen atom or an organic group with 1 to 10 carbon atoms, and * denotes the position of bonding to the carbon atom to which $R^5$ is bonded in Formula (3), or a phenylene group, $R^7$ represents a divalent organic group with 1 to 8 carbon atoms, and X represents a monovalent group represented by Formula (4-1):

(4-1)

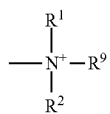

where $R^1$ and $R^2$ each independently represents a hydrocarbon group comprising 1 to 10 carbon atoms, and $R^9$ represents a hydrocarbon group with 1 to 10 carbon atoms, and the repeating unit (B) comprises a group represented by Formula (2) in a side chain thereof

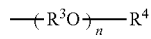
(2)

where $R^3$ represents an alkanediyl group comprising 2 to 8 carbon atoms, $R^4$ represents a hydrogen atom or an organic group comprising 1 to 40 carbon atoms, and n has an average value of 1 or more.

4. The method according to claim 3, wherein:
said surface formed of an inorganic material is a glass surface;
$R^6$ represents *—(C=O)—O— or *—(C=O)—NR$^8$—, and $R^7$ represents a divalent hydrocarbon group with 1 to 8 carbon atoms;
a content of repeating unit (A) is 0.01 - 20% by mass;
repeating unit (B) consists of a repeating unit represented by Formula (5):

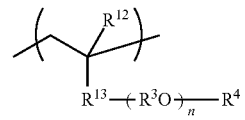
(5)

where
$R^{12}$ represents a hydrogen atom or a methyl group,
$R^{13}$ represents a phenylene group, —O—, —(C=O)—O—, —(C=O)—NR$^{14}$—, or —NR$^{14}$—(C=O)—, where $R^{14}$ represents a hydrogen atom or an organic group comprising 1 to 10 carbon atoms, and  denotes a position of bonding to a carbon atom to which $R^{12}$ is bonded in the Formula (5), and
$R^3$ represents an alkanediyl group comprising 2 to 8 carbon atoms, $R^4$ represents a hydrogen atom or an organic group comprising 1 to 40 carbon atoms, and n has an average value of 1 or more; and
a content of repeating unit (B) is 30 - 99.99% by mass.

* * * * *